US00PP10769P

United States Patent [19]

Hoy, Jr.

[11] Patent Number: Plant 10,769

[45] Date of Patent: Feb. 2, 1999

[54] HYBRID TEA ROSE PLANT NAMED 'HILRAZ'

[75] Inventor: Lowell Leslie Hoy, Jr., Richmond, Ind.

[73] Assignee: DeVor Nurseries, Inc., Watsonville, Calif.

[21] Appl. No.: 931,920

[22] Filed: Aug. 14, 1997

[51] Int. Cl.[6] ..... A01H 5/00

[52] U.S. Cl. ..... Plt./19

[58] Field of Search ..... Plt./19, 18, 20

[56] References Cited

U.S. PATENT DOCUMENTS

| | | | |
|---|---|---|---|
| P.P. 5,360 | 12/1984 | Hoy, Jr. | Plt./18 |
| P.P. 6,909 | 7/1989 | Kvaskoff | Plt./19 |
| P.P. 8,342 | 8/1993 | Meilland | Plt./19 |

*Primary Examiner*—Howard J. Locker

*Attorney, Agent, or Firm*—Christie, Parker & Hale, LLP

[57] ABSTRACT

A new and distinct cultivar of hybrid tea rose plant producing deep pink flowers of good form.

1 Drawing Sheet

BACKROUND OF THE INVENTION

The present invention relates to a new and distinct hybrid tea rose variety which was originated by my crossing as seed parent an unnamed and undistributed seedling and as pollen parent the variety known as 'Lady Diana' (U.S. Plant Pat. No. 5,360. The varietal denomination of this new rose is 'Hilraz'.

SUMMARY OF THE INVENTION

Among the novel characteristics possessed by the new variety which distinguish it from its parents and all other varieties of which I am aware are its attractive bud and flower form and consistent flower color.

Asexual reproduction by budding of the new variety as performed in Watsonville, Calif., shows that the foregoing and other distinguishing characteristics come true to form and are established and transmitted through succeeding propagations. Other known forms of asexual reproduction may be also used.

COMPARISON WITH PARENTS

'Hilraz' has more upright growth habit than its seed parent and darker pink flower color than its pollen parent.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—'Lady Diana'.

Class: Hybrid tea.

The following is a detailed description of the new variety, from specimens grown in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:

(1) *Size.*—Medium.

(2) *Form.*—Ovate.

(3) *Color.*—When sepals first divide, bud color is near 51A.

(4) *Sepals.*—Longer than bud, about 3 cm to 3.5 cm long, sepals spread and reflex when bloom opens and ages; some sepals are foliaceous with leaf-shaped ends. Color: Near 144B with tinges of near 146C in center.

(5) *Peduncle.*—Length: About 6.5 to 8 cm. Aspect: Smooth. Strength: Erect, sturdy. Color: Near 144.

(6) *Bracts.*—Usually one, near 148B, broadly lanceolate, about 6.5 to 7 cm below calyx.

B. Bloom:

(1) *Size.*—Average size when fully expanded about 9 cm to 10 cm.

(2) *Borne.*—Singly.

(3) *Form.*—Imbricated, outer petals reflex to points, inner petals roll under.

(4) *Petalage.*—Number of petals under normal conditions — about 21 to 25.

(5) *Color (⅓ to ½ open).*—Outer petals — Top surface near 66D, under surface near 62A. Inner Petals — Top surface near 66C, under surface near 66D. Base of petals — Near 1C. General tonality from a distance: Deep pinks.

(6) *Color (fully open).* Outer petals — Top surface near 66C, under surface near 67D. Inner petals — Top surface near 66C, under surface near 66D. Base of petals: Near 1C. General tonality from a distance: Pinks.

(7) *Color change.*—Retains color well though color may lighten very slightly. Petal top surface: Near 66C. Petal under surface: Near 66D. General tonality at a distance: Pink.

C. Petals:

(1) *Texture.*—Thick, smooth.

*Appearence.*—Matte inside and outside.

(3) *Forms.*—Orbicular with ruffled edging.

(4) *Arrangement.*—Imbricated.

(5) *Petaloids.*—Few, 2 to 3.

(6) *Fragrance.*—Slightly spicy.

(7) *Lasting quality.*—On plant about 12 to 14 days, after cutting about 7 to 10 days.

(8) *Persistence.*—Petals drop off cleanly.

Reproductive organs

A. Stamens:
(1) *Arrangement.*—Regularly arranged around styles.
(2) *Anthers.*—Near 16B.
(3) *Filaments.*—Near 5OD.
(4) *Pollen.*—Near 17B.

B. Pistils:
(1) *Styles.*—Bunched, uneven, thin.
(2) *Stigmas.*—Near 159A.

C. Characteristics of hips: Not observed.

Plant

A. Form: Upright.

B. Growth: Very vigorous; about 167 cm to about 182 cm in height at first season.

C. Foliage: Compound 3 and 5 leaflets
(1) *Size.*—Medium.
(2) *Quantity.*—Abundant
(3) *Color.*—New foliage near 146A with edging near 183C on serration; under side near 148B with near 183C on veining; mature foliage upper side near 147A, under side near 147B.
(4) *Shape.*—Oval.
(5) *Texture.*—Upper side leathery; under side leathery, veined.
(6) *Edge.*—Serrated.
(7) *Serration.*—Denticulate.
(9) *Stipules.*—Medium, slightly bearded margins, adnate with enlarged area in middle.
(10) *Rachis.*—Small prickles on under side.
(11) *Petioles.*—Top near 146A, under side near 146C.
(12) *Auricle.*—Spreading outwardly, slightly bearded margins.
(13) *Resistance to disease.*—Very resistant to blackspot, mildew and rust.

D. Wood:
(1) *New wood.*—Color near 146B, bark smooth
(2) *Old wood.*—Color near 146A, bark smooth.

E. Flower stem: About 55 cm to about 66 cm from last cut.

F. Thorns:
(1) *Thorns.*—Quantity: On main stalk, few; laterals from stalk, few, Form: Slightly curved downward. Length: About 0.8 to 1 cm. Color: Near 183C with slight near 146D tinges throughout (when young). Position: Irregular.
(2) *Prickles.*—None.

G. Winter hardiness: Winter hardy in Watsonville, Calif.

I claim:

1. A new and distinct cultivar of hybrid tea rose plant, substantially as shown and described.

* * * * *

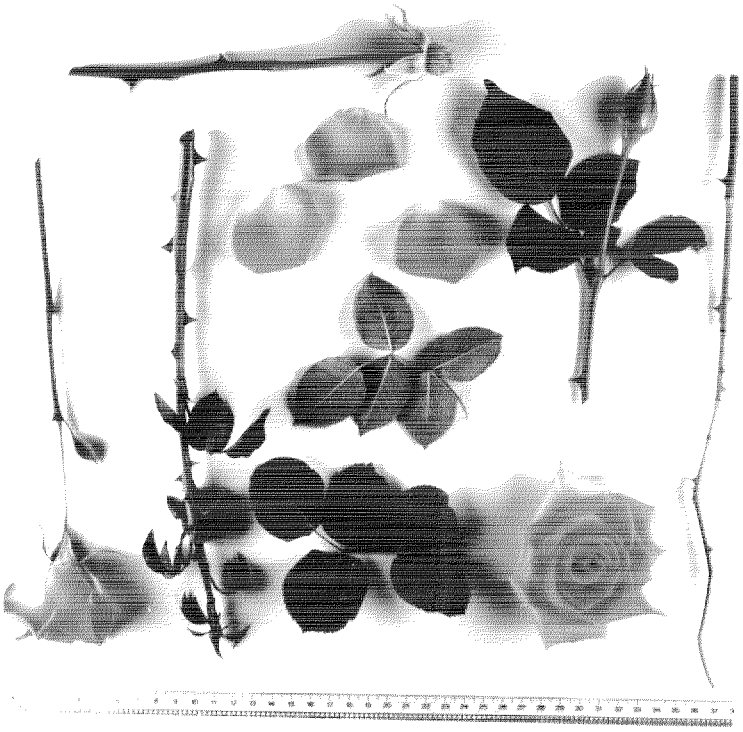

UNITED STATES PATENT AND TRADEMARK OFFICE

CERTIFICATE OF CORRECTION

PATENT NO. : Plant 10,769
DATED : February 2, 1999
INVENTOR(S) : Lowell Leslie Hoy, Jr.

It is certified that error appears in the above-identified patent and that said Letters Patent is hereby corrected as shown below:

Column 2, line 15, change "Near 144" to -- Near 144A –.
Column 2, line 42, replace "*Appearence.*—" with -- (2) *Appearance.*— –.

Signed and Sealed this

Sixth Day of June, 2000

*Attest:*

Q. TODD DICKINSON

*Attesting Officer*

*Director of Patents and Trademarks*